(12) United States Patent
Okada et al.

(10) Patent No.: US 9,376,375 B2
(45) Date of Patent: Jun. 28, 2016

(54) METHOD FOR PRODUCING OXIME

(75) Inventors: Masahide Okada, Ube (JP); Junichi Kugimoto, Ube (JP); Kazunori Kurosawa, Ube (JP); Joji Funatsu, Ube (JP); Katsuyoshi Kudo, Ube (JP)

(73) Assignee: UBE INDUSTRIES, LTD., Ube-Shi (JP)

( * ) Notice: Subject to any disclaimer, the term of this patent is extended or adjusted under 35 U.S.C. 154(b) by 50 days.

(21) Appl. No.: 13/636,433

(22) PCT Filed: Mar. 23, 2011

(86) PCT No.: PCT/JP2011/057018
§ 371 (c)(1),
(2), (4) Date: Sep. 21, 2012

(87) PCT Pub. No.: WO2011/118647
PCT Pub. Date: Sep. 29, 2011

(65) Prior Publication Data
US 2013/0023697 A1 Jan. 24, 2013

(30) Foreign Application Priority Data
Mar. 24, 2010 (JP) ................................. 2010-067479

(51) Int. Cl.
C07C 249/08 (2006.01)

(52) U.S. Cl.
CPC ........... *C07C 249/08* (2013.01); *C07C 2101/20* (2013.01)

(58) Field of Classification Search
None
See application file for complete search history.

(56) References Cited

U.S. PATENT DOCUMENTS

| 3,808,275 | A | * | 4/1974 | Hirose et al. ................... 564/259 |
| 5,300,689 | A | * | 4/1994 | Krbechek et al. ............ 564/259 |
| 5,434,307 | A | * | 7/1995 | Nwaonicha et al. .......... 564/259 |
| 5,488,161 | A |   | 1/1996 | Krbechek |
| 2003/0100795 | A1 |   | 5/2003 | Herwig et al. |
| 2010/0267944 | A1 | * | 10/2010 | Kugimoto et al. ............ 540/464 |
| 2011/0092699 | A1 |   | 4/2011 | Iwahama et al. |

FOREIGN PATENT DOCUMENTS

| JP | A-H02-025457 | 1/1990 |
| JP | A-H07-504912 | 6/1995 |
| JP | A-2004-059553 | 2/2004 |
| JP | A-2006-206476 | 8/2006 |
| JP | A-2009-298706 | 12/2009 |
| JP | A-2010-006775 | 1/2010 |
| WO | WO 93/19041 | 9/1993 |
| WO | WO 2009/069522 A1 | 6/2009 |
| WO | WO 2009069522 | * 6/2009 |

OTHER PUBLICATIONS

Michael Castellani, Marshall University, Chemistry 204 Lecture Notes for Chapter 15, 2002, http://science.marshall.edu/castella/chm204/chap15.pdf.*
International Preliminary Report on Patentability, issued on Sep. 25, 2012, for International application No. PCT/JP2011/057018.
Office Action issued in Chinese Patent Application No. 201180025500.5 on Jan. 10, 2014.
Second Notification of Office Action issued in Chinese Patent Application No. 201180025500.5 on Aug. 26, 2014.
Office Action in European Patent Application No. 11 759 452.3, dated Feb. 9, 2015.
Oliver E. Hutt et al; "Synthesis of Skeletally Diverse and Stereochemically Complex Library Templates Derived from Isosteviol and Steviol" Organic Letters, vol. 15, No. 7, Apr. 5, 2013, Web publication date: Mar. 26, 2013, pp. 1602-1605.

* cited by examiner

*Primary Examiner* — Fereydoun G Sajjadi
*Assistant Examiner* — Jennifer C Sawyer
(74) *Attorney, Agent, or Firm* — Knobbe Martens Olson & Bear LLP

(57) ABSTRACT

This invention relates to a process for producing an oxime comprising reacting a ketone and hydroxylamine in the presence of a carboxylic acid and/or its salt in a system consisting of an aqueous phase and a hydrophobic solvent phase.

4 Claims, No Drawings

METHOD FOR PRODUCING OXIME

This application is the U.S. National Phase under 35 U.S.C. §371 of International Application No. PCT/JP2011/057018, filed Mar. 23, 2011, designating the U.S., and published in Japanese as WO2011/118647 on Sep. 29, 2011, which claims priority to Japanese Patent Application No. 2010-067479, filed Mar. 24, 2010, the entire content of which is incorporated herein by reference.

TECHNICAL FIELD

The present invention relates to a process for producing a corresponding oxime from a ketone and hydroxylamine.

An oxime can be converted into an amide compound by Beckmann rearrangement reaction, particularly an oxime derived from a cyclic ketone can be converted into a lactam. For example, cyclohexanone oxime gives ε-caprolactam which is a starting material for Nylon 6 and cyclododecanone oxime gives laurolactam which is a starting material for Nylon 12.

BACKGROUND ART

Known processes for producing an oxime are as follows.

(i) A process where in the presence of a N-hydroxyimide compound and a compound produced by introducing a protecting group (for example, an acyl group such as an acetyl group) into a hydroxyl group in the N-hydroxyimide compound, a compound having a methyl or methylene group is reacted with a nitrous acid ester or nitrite (Patent Reference No. 1). Here, the N-hydroxyimide compound is derived from an aliphatic polyvalent carboxylic anhydride (cyclic anhydride) such as N-hydroxysuccinimide or an aromatic polyvalent carboxylic anhydride (cyclic anhydride).

(ii) A process where a cycloalkane or the like is photonitrosated (Patent Reference No. 2).

(iii) A process where in the presence of a catalyst such as titanosilicate, a ketone, ammonia and hydrogen peroxide are reacted (Patent Reference No. 3).

(iv) A process where a corresponding ketone is condensed with a hydroxylamine produced by metathesis of a hydroxylamine sulfate mineral acid salt.

Among these, the process (iv) is versatile and common. For example, cyclododecanone oxime as a starting material for laurolactam is produced by reacting cyclododecanone with a hydroxylamine mineral acid salt (Patent Reference No. 4).

According to the process (iv), in the production of an oxime, the use of hydrophobic solvent is advantageous in the light of an easier oil/aqueous separation and solvent recovery, and desirable in the light of an influence of water on subsequent Beckmann rearrangement of the oxime can be reduced (Patent Reference No. 5). However, when an oxime is produced from a ketone and hydroxylamine in a biphasic system of a hydrophobic solvent and water, the reaction takes a long time. In particular, when a ketone which is less easily distributed into an aqueous phase is used in oxime-forming, the reaction tends to take a longer time. This leads to need a larger apparatus and thus enormous equipment expenses, which is disadvantageous in the light of productivity and economy.

PRIOR ART REFERENCES

Patent References

Patent Reference No. 1: Japanese laid-open patent publication No. 2009-298706.
Patent Reference No. 2: Japanese laid-open patent publication No. 2010-6775.
Patent Reference No. 3: Japanese laid-open patent publication No. 2006-206476.
Patent Reference No. 4: Japanese laid-open patent publication No. 2004-59553.
Patent Reference No. 5: International Publication No. WO 09/069,522.

Problem to be Solved by the Invention

An objective of the present invention is to solve the above problem of a reaction time in a process for industrially producing a corresponding oxime from a ketone and hydroxylamine in a biphasic system of a hydrophobic solvent and water and to achieve the size reduction of an apparatus.

Means for Solving Problem

We have intensely investigated the oxime-formation reaction of a ketone and have found that adding a carboxylic acid and/or its salt can properly accelerate the reaction, achieving the present invention.

Specifically, the present invention relates to the followings.

[1] A process for producing an oxime comprising reacting a ketone and hydroxylamine in the presence of a carboxylic acid and/or its salt in a system consisting of an aqueous phase and a hydrophobic solvent phase.

[2] The process as described in [1], wherein the ketone has 8 or more and 30 or less carbon atoms.

[3] The process as described in [1], wherein the ketone is cyclododecanone.

[4] The process as described in [1], wherein the carboxylic acid and/or its salt have 5 or more carbon atoms.

[5] The process as described in [1], wherein a hydrogen ion concentration (pH) of the aqueous phase during the reaction is in the range of pH 5 to pH 6.

[6] The process as described in [1], wherein the hydrophobic solvent is an aromatic or aliphatic hydrocarbon.

Advantage of the Invention

The present invention can provide a process for producing an oxime from a ketone and hydroxylamine in a biphasic system of a hydrophobic solvent and water, whereby its reaction is accelerated and allows for the size reduction of a reaction apparatus.

MODE FOR CARRYING OUT THE INVENTION

There will be detailed the present invention.

The present invention relates to a process for producing an oxime from a ketone and hydroxylamine in the presence of a carboxylic acid and/or its salt in a biphasic system of a hydrophobic solvent and water. First, compounds used for the process for producing an oxime of the present invention will be described.

Carboxylic Acid or its Salt

A process for producing an oxime of the present invention is characterized in that a carboxylic acid and/or its salt are used. A rate of an oxime-formation reaction is increased by conducting the reaction in the presence of a carboxylic acid and/or its salt. As described later, when a ketone which is easier distributed into a hydrophobic solvent phase than an aqueous phase (hereinafter, sometimes referred to as a "highly hydrophobic ketone") in the production of an oxime according to the present invention is used, the rate of the reaction is more significantly increased. When a highly hydrophobic ketone is used, a reaction field of the oxime-formation is in the oil phase, and therefore, a carboxylic acid or its salt combined is also preferably a carboxylic acid or its salt which is easily to be distributed into a hydrophobic solvent phase. The use of a carboxylic acid or its salt allows hydroxylamine present in the aqueous phase to easily mass-transfer into the oil phase as a reaction field, resulting in increase in the rate of the oxime-formation reaction.

A carboxylic acid or its salt used in the present invention is preferably, but not limited to, a saturated or unsaturated linear aliphatic carboxylic acid having 5 or more carbon atoms, an aromatic carboxylic acid or a salt thereof. A carboxylic acid having 4 or less carbon atoms such as acetic acid and propionic acid is highly soluble in water and is easily distributed into an aqueous phase in an oxime-formation reaction, so that it is not prominently effective for increasing the rate of the oxime-formation reaction. There are no particular restrictions to the upper limit of the carbon number of a carboxylic acid, but the carboxylic acid having more than 28 carbon atoms is less soluble in the reaction solvent. Examples of a specifically preferable carboxylic acid include saturated aliphatic monocarboxylic acids such as caproic acid, capric acid, undecanoic acid, lauric acid, palmitic acid, stearic acid and arachic acid; saturated aliphatic dicarboxylic acids such as sebacic acid and dodecanedioic acid; unsaturated aliphatic carboxylic acids such as oleic acid, linoleic acid and linolenic acid; and aromatic carboxylic acids such as benzoic acid, phthalic acid and naphthoic acid.

Examples of a salt of a carboxylic acid include salts of the above carboxylic acid with an alkali metal (for example, sodium and potassium) or an alkaline earth metal (for example, magnesium and calcium). Specific examples include sodium laurate and calcium laurate.

The above carboxylic acid or the salts thereof can be used in combination of two or more.

Ketone

In the present invention, an oxime-formation reaction is conducted in a biphasic system of a hydrophobic solvent phase and an aqueous phase. When a ketone which is easily distributed into the aqueous phase is used, a reaction rate is relatively larger because an oxime-formation also proceeds in the aqueous phase, which means addition of a carboxylic acid or its salt is relatively less effective for increasing the rate of reaction. When a highly hydrophobic ketone is used, a reaction field is limited to an oil phase, so that a mass-transfer rate of hydroxylamine to an oil phase makes the rate-determining step. Addition of a carboxylic acid or its salt increases the mass-transfer rate, so that when a highly hydrophobic ketone is used, the effect of the present invention (i.e. the effect of increasing the rate of the oxime-formation by the addition of a carboxylic acid or its salt) becomes more prominent. That is, when a highly hydrophobic ketone is desirably used, the present invention is particularly important.

A ketone in the present invention can be a compound represented by formula (1).

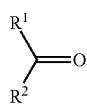

(1)

wherein each of $R^1$ and $R^2$ represents an organic group, or $R^1$ and $R^2$ together may represent a divalent organic group, whereby forming a ring with a carbon atom to which $R^1$ and $R^2$ attach.

In the present invention, the use of a ketone where the total carbon number of $R^1$ and $R^2$ is preferably 8 or more, more preferably 8 or more and 30 or less is preferable because it is easily distributed into a hydrophobic solvent in an oxime-formation step.

The organic group for $R^1$ and $R^2$ can be, for example, alkyl, alkenyl, alkynyl, cycloalkyl, cycloalkenyl, aryl, aralkyl, or aromatic or non-aromatic heterocycle.

An alkyl group can be, for example, alkyl having 1 to 20 carbon atoms, preferably alkyl having 1 to 12 carbon atoms, further preferably alkyl having 2 to 8 carbon atoms. Specific examples include methyl, ethyl, propyl, isopropyl, butyl, isobutyl, s-butyl, t-butyl, pentyl, isopentyl, hexyl, isohexyl, heptyl, octyl, nonyl, decyl, dodecyl and pentadecyl.

An alkenyl group can be, for example, alkenyl having 2 to 20 carbon atoms, preferably alkenyl having 2 to 12 carbon atoms, further preferably alkenyl having 2 to 8 carbon atoms. Specific examples include vinyl, allyl, 1-propenyl, 1-butenyl, 1-pentenyl and 1-octenyl.

An alkynyl group can be, for example, alkynyl having 2 to 20 carbon atoms, preferably alkynyl having 2 to 12 carbon atoms, further preferably alkynyl having 2 to 8 carbon atoms. Specific examples include ethynyl and 1-propynyl.

A cycloalkyl group can be, for example, cycloalkyl having 3 to 20 carbon atoms, preferably cycloalkyl having 3 to 15 carbon atoms. Specific examples include cyclopropyl, cyclobutyl, cyclopentyl, cyclohexyl, cycloheptyl, cyclooctyl and cyclododecyl.

A cycloalkenyl group can be, for example, cycloalkenyl having 3 to 20 carbon atoms, preferably cycloalkenyl having 3 to 15 carbon atoms. Specific examples include cyclopentenyl, cyclohexenyl and cyclooctenyl.

Examples of an aryl group include phenyl and naphthyl.
Examples of an aralkyl group include benzyl, 2-phenylethyl and 3-phenylpropyl.

Examples of an aromatic or non-aromatic heterocyclic group include 2-pyridyl, 2-quinolyl, 2-furyl, 2-thienyl and 4-piperidinyl.

When $R^1$ and $R^2$ together represent a divalent organic group, they form a ring with a carbon atom to which they are attached. A divalent organic group can be linear or branched alkylene, preferably linear alkylene. In the present invention, when the ring is an 8 or more membered ring, which is easily distributed into a hydrophobic solvent in an oxime-formation step, the present invention is prominently effective. The present invention is particularly effective when a ring formed is, for example, an 8 to 30-membered ring, preferably an 8 to 20-membered ring, further preferably an 8 to 14-membered ring.

Regardless of ring formation, these organic groups can have various substituents without limitations as long as they do not inhibit the reaction. Examples of a substituent include halogen, oxo, mercapto, substituted oxy such as alkoxy, aryloxy and acyloxy, substituted thio, substituted oxycarbonyl, substituted or unsubstituted carbamoyl, cyano, nitro, substituted aminoalkyl, alkenyl, alkynyl, cycloalkyl, cycloalkenyl, aryl such as phenyl and naphthyl, aralkyl and heterocyclic group.

Among ketones represented by formula (1), examples of a ketone by which the present invention is prominently effective include 1-cyclohexyl-1-propanone, acetophenone, benzophenone and 4-hydroxyacetophenone, and examples of a ring-forming ketone include cyclooctanone, cyclononanone, cyclodecanone, cycloundecanone, cyclododecanone, cyclotridecanone, cyclotetradecanone, cyclopentadecanone, cyclohexadecanone, cyclooctadecanone and cyclononadecanone. Among these, cyclododecanone is industrially very important.

Hydroxylamine

Since hydroxylamine is unstable, it is produced and sold as an aqueous solution of an inorganic salt of hydroxylamine such as an aqueous solution of hydroxylamine sulfate or hydroxylamine carbonate. Usually, before the use in the reaction, a base such as aqueous ammonia is added to the solution to liberate hydroxylamine. In the present invention, an aqueous solution of hydroxylamine in which hydroxylamine has preliminarily liberated, can be used, but usually, in a reaction apparatus, an aqueous solution of a hydroxylamine inorganic acid salt (preferably, sulfate salt) and a base (preferably aqueous ammonia) are charged to liberate hydroxylamine in the reaction apparatus.

Hydrophobic Solvent

In the process for producing an oxime of the present invention, a hydrophobic solvent is used. Therefore, the process for producing an oxime of the present invention is conducted in a biphasic system of water derived from the above aqueous solution of hydroxylamine and a hydrophobic solvent.

There are no particular restrictions to a hydrophobic solvent, but a hydrophobic solvent in which a ketone as a starting material and an oxime to be produced are highly dissolvable are preferable. Specific examples include aliphatic hydrocarbons such as hexane, heptane, octane, cyclododecane and isopropyl cyclohexane; aromatic hydrocarbons such as benzene, toluene and xylene; halogenated hydrocarbons such as chloroform, dichloromethane, dichloroethane, carbon tetrachloride, chlorobenzene and trifluoromethylbenzene; nitro compounds such as nitrobenzene, nitromethane and nitroethane; fluoroalcohols such as hexafluoroisopropyl alcohol and trifluoroethanol; and mixtures thereof.

The oxime prepared by the production process of the present invention can be used in the Beckmann rearrangement reaction for producing an amide compound, particularly a lactam, and preferably the same solvent as that used in the oxime production is used in the Beckmann rearrangement reaction because the necessity for solvent exchange can be eliminated. When an identical solvent is used in production of an oxime and in the Beckmann rearrangement reaction, and thionyl chloride is used as a catalyst in the Beckmann rearrangement reaction, the use of an alcohol or an ester as a solvent is undesirable because it adversely affects the Beckmann rearrangement reaction.

Oxime-Formation Reaction

There will be described a process for producing an oxime using the above compound. In the process for producing an oxime of the present invention, a ketone and hydroxylamine are reacted in the presence of a carboxylic acid and/or its salt in a biphasic system of an aqueous phase and a hydrophobic solvent.

There are no particular restrictions to a quantitative ratio of a ketone and hydroxylamine, and preferably they react in an equimolar ratio. When a ketone and hydroxylamine are used in an equimolar ratio and a plurality of reaction apparatuses are serially connected for continuous reaction, then the ketone and hydroxylamine are fed by countercurrent feeding. Specifically, it is preferable embodiment that a reaction process where a ketone is fed to the first reaction tank, a light liquid phase (oil phase) containing a ketone and an oxime formed by the reaction is sequentially fed to the subsequent reaction tank, while hydroxylamine is fed to the last reaction tank, and a heavy liquid phase containing hydroxylamine is sequentially fed to the previous reaction tank, and the method leads to the reduction of an unreacted ketone and/or hydroxylamine.

The use amount of a carboxylic acid or its salt is, but not limited to, preferably 0.001 mol % to 5 mol %, more preferably 0.01 mol % to 1 mol % based on the ketone. If the amount is too small, it is less effective for increasing the rate of the oxime-formation reaction. If an excessive amount is added, additional effect for increasing the rate of the oxime-formation reaction is not achieved.

A reaction temperature is preferably 115° C. or less, more preferably 100° C. or less, further preferably 75° C. or higher and 100° C. or lower. Although a higher reaction temperature is preferable in terms of maintaining an industrially suitable reaction rate, an excessively high temperature is dangerous because of the decomposition of hydroxylamine. Furthermore, since hydroxylamine is supplied as an aqueous solution, a reaction at a high temperature requires a pressurized vessel. Therefore, a temperature of 100° C. or lower is convenient because the reaction can be conducted under an ambient pressure.

A hydrogen ion concentration (pH) of the aqueous phase in the oxime-formation reaction is preferably pH 5 or more and 6 or less. The higher the pH is, the higher a concentration of liberated hydroxylamine is, resulting in a higher reaction rate. Therefore, a higher pH is preferable in terms of maintaining an industrially suitable reaction rate. A too low pH is undesirable because a reaction rate is industrially inadequate. Meanwhile, once being liberated, hydroxylamine is so unstable that it self-decomposes. Therefore, from the point of view of safety, retention of hydroxylamine in a high concentration must be avoided. Hydroxylamine liberated in the aqueous phase moves to the oil phase and is consumed by the oxime-formation reaction. In the present invention, addition of a carboxylic acid or its salt accelerates mass transfer of hydroxylamine into the oil phase, leading to increase in a rate of consumption of hydroxylamine, and in the aqueous phase, therefore, a pH of 6 or less can be permitted.

A pH is adjusted by addition of a base (preferably, aqueous ammonia). For example, a pH is adjusted by adding a base in a proper amount such that a pH does not exceed a desired value while a pH of the aqueous phase is constantly monitored by a pH controller.

A reaction apparatus used for the oxime-formation reaction can be a common reaction apparatus such as a batch type reaction apparatus, a tubular continuous reaction apparatus and a continuous stirred tank flow reactor, and for maintaining a reaction rate suitable for industrial production, a batch type reaction apparatus or a continuous stirred tank flow reactor, which has a mixing device capable of adequately mixing a hydrophobic solvent and an aqueous phase, is preferable.

A reaction time varies depending on a ketone, the type of a solvent, a concentration of a ketone, a molar ratio of a ketone and hydroxylamine, a reaction temperature, a pH and so on, and preferably, in the light of the prevention of increase in an apparatus size, the conditions are set such that a reaction time becomes 15 hours or less. In the present invention, there is a possibility that a reaction time may be over 15 hours, but when the above carboxylic acid and/or its salt are used, a reaction time is reduced compared with the case where these are absent.

The oxime-formation reaction can be conducted in the air, but a reaction system can be filled with an inert gas such as nitrogen or argon.

The oxime-formation reaction can be conducted under pressure, but a pressurized reaction apparatus is more expensive than an ambient-pressure reaction apparatus and thus economically disadvantageous. The reaction is, therefore, conducted under an ambient pressure.

An oxime generated by the above reaction can be obtained by separating an organic phase from the reaction mixture and then completely or partly removing a solvent, but the oxime remaining dissolved in the solvent can be used in the subsequent Beckmann rearrangement reaction.

The type of the oxime produced by the above process corresponds to the type of the ketone used; for example, when cyclododecanone is used, cyclododecanone oxime is produced.

EXAMPLES

There will be described the present invention with reference to, but not limited to, Examples. Cyclododecanone and hydroxylamine in a reaction solution were analyzed by gas chromatography and by titration, respectively, and from the results obtained, conversions of cyclododecanone and hydroxylamine were calculated. Examples involve a batch experiment comparing reaction times of an oxime-formation reaction in individual tanks in a countercurrent two-tank continuous-flow reaction, where an initial concentration in each batch reaction corresponds to an inlet concentration in each tank in the countercurrent continuous reaction.

Example 1

In a 1 liter-volume vertical reactor was placed 1162.0 g of a 15% by weight aqueous solution of hydroxylamine sulfate, and while maintaining the solution at 40° C. or lower, a 25% by weight aqueous ammonia was added dropwise to make a pH 4, to prepare 1313.1 g of an aqueous solution of hydroxylamine.
(First Tank, the Tank of Excessive Cyclododecanone)
In a 1 liter-volume vertical reactor were placed 339.7 g of the above aqueous solution of hydroxylamine, 167.3 g of cyclododecanone, 0.104 g of caproic acid and 71.9 g of toluene, and then, a 25% by weight aqueous ammonia was added dropwise to the mixture at 90° C. so that a pH of the aqueous phase is maintained at 5.8, and the oxime-formation reaction was conducted until a concentration of hydroxylamine sulfate in the aqueous phase became 0.1% by weight or less. A reaction time was 4 hours (a conversion of hydroxylamine: 99.2%).

At the end of the reaction, the aqueous phase was drained while the organic phase was used as it is, in the reaction in the second tank described below.
(Second Tank, the Tank of Excessive Hydroxylamine)
To the above organic phase was further added 567.4 g of the above aqueous solution of hydroxylamine, and then, while a 25% by weight aqueous ammonia was added dropwise at 90° C. to keep a pH of the aqueous phase 5.8, the reaction was conducted until a concentration of cyclododecanone in the organic phase became 0.1% by weight or less. A reaction time was 7 hours (a conversion of cyclododecanone: 99.8%).

Example 2

A process was conducted as described in Example 1, except for substituting undecanoic acid for caproic acid.
(First Tank, the Tank of Excessive Cyclododecanone)
An oxime-formation reaction was conducted until a concentration of hydroxylamine sulfate in an aqueous phase became 0.1% by weight or less. A reaction time was 4 hours (a conversion of hydroxylamine: 99.2%).
(Second Tank, the Tank of Excessive Hydroxylamine)
The reaction was conducted until a concentration of cyclododecanone in an organic phase became 0.1% by weight or less. A reaction time was 6 hours (a conversion of cyclododecanone: 99.8%).

Example 3

A process was conducted as described in Example 1, except for substituting lauric acid for caproic acid.
(First Tank, the Tank of Excessive Cyclododecanone)
An oxime-formation reaction was conducted until a concentration of hydroxylamine sulfate in an aqueous phase became 0.1% by weight or less. A reaction time was 4 hours (a conversion of hydroxylamine: 99.2%).
(Second Tank, the Tank of Excessive Hydroxylamine)
The reaction was conducted until a concentration of cyclododecanone in an organic phase became 0.1% by weight or less. A reaction time was 6 hours (a conversion cyclododecanone of: 99.8%).

Example 4

A process was conducted as described in Example 1, except for substituting dodecanedioic acid for caproic acid.
(First Tank, the Tank of Excessive Cyclododecanone)
An oxime-formation reaction was conducted until a concentration of hydroxylamine sulfate in an aqueous phase became 0.1% by weight or less. A reaction time was 4 hours (a conversion of hydroxylamine: 99.2%).
(Second Tank, the Tank of Excessive Hydroxylamine)
The reaction was conducted until a concentration of cyclododecanone in an organic phase became 0.1% by weight or less. A reaction time was 6 hours (a conversion of cyclododecanone: 99.8%).

Example 5

A process was conducted as described in Example 1, except for substituting stearic acid for caproic acid.
(First Tank, the Tank of Excessive Cyclododecanone)
An oxime-formation reaction was conducted until a concentration of hydroxylamine sulfate in an aqueous phase became 0.1% by weight or less. A reaction time was 4 hours (a conversion of hydroxylamine: 99.2%).
(Second Tank, the Tank of Excessive Hydroxylamine)
The reaction was conducted until a concentration of cyclododecanone in an organic phase became 0.1% by weight or less. A reaction time was 6 hours (a conversion of cyclododecanone: 99.8%).

Example 6

A process was conducted as described in Example 5, except that the amount of stearic acid was 1.305 g in place of 0.261 g.
(First Tank, the Tank of Excessive Cyclododecanone)
An oxime-formation reaction was conducted until a concentration of hydroxylamine sulfate in an aqueous phase became 0.1% by weight or less. A reaction time was 2 hours (a conversion of hydroxylamine: 99.2%).
(Second Tank, the Tank of Excessive Hydroxylamine)
The reaction was conducted until a concentration of cyclododecanone in an organic phase became 0.1% by weight or less. A reaction time was 3 hours (a conversion of cyclododecanone: 99.8%).

Example 7

A process was conducted as described in Example 1, except for substituting sodium laurate for caproic acid.
(First Tank, the Tank of Excessive Cyclododecanone)
An oxime-formation reaction was conducted until a concentration of hydroxylamine sulfate in an aqueous phase became 0.1% by weight or less. A reaction time was 4 hours (a conversion of hydroxylamine: 99.2%).
(Second Tank, the Tank of Excessive Hydroxylamine)
The reaction was conducted until a concentration of cyclododecanone in an organic phase became 0.1% by weight or less. A reaction time was 6 hours (a conversion of cyclododecanone: 99.8%).

Example 8

A process was conducted as described in Example 1, except for substituting propionic acid for caproic acid.
(First Tank, the Tank of Excessive Cyclododecanone)
The reaction was conducted until a concentration of hydroxylamine sulfate in an aqueous phase became 0.1% by weight or less. A reaction time was 6 hours (a conversion of hydroxylamine: 99.2%).
(Second Tank, the Tank of Excessive Hydroxylamine)
The reaction was conducted until a concentration of cyclododecanone in an organic phase became 0.1% by weight or less. A reaction time was 9 hours (a conversion of cyclododecanone: 99.8%).

Comparative Example 1

A process was conducted as described in Example 1, except that caproic acid was not added.
(First Tank, the Tank of Excessive Cyclododecanone)
The reaction was conducted until a concentration of hydroxylamine sulfate in an aqueous phase became 0.1% by weight or less. A reaction time was 8 hours (a conversion of hydroxylamine: 99.2%).
(Second Tank, the Tank of Excessive Hydroxylamine)
The reaction was conducted until a concentration of cyclododecanone in an organic phase became 0.1% by weight or less. A reaction time was 9 hours (a conversion of cyclododecanone: 99.8%).

Comparative Example 2

A process was conducted as described in Example 1, except for substituting tetrabutylammonium hydrogen sulfate for caproic acid.
(First Tank, the Tank of Excessive Cyclododecanone)
The reaction was conducted until a concentration of hydroxylamine sulfate in an aqueous phase became 0.1% by weight or less. A reaction time was 10 hours (a conversion of hydroxylamine: 99.2%).
(Second Tank, the Tank of Excessive Hydroxylamine)
The reaction was conducted until a concentration of cyclododecanone in an organic phase became 0.5% by weight or less. A reaction time was 7 hours (a conversion of cyclododecanone: 99.0%).

Example 9

A process was conducted as described in Example 5, except that a solvent was isopropylcyclohexane.
(First Tank, the Tank of Excessive Cyclododecanone)
The reaction was conducted until a concentration of hydroxylamine sulfate in an aqueous phase became 0.1% by weight or less. A reaction time was 7 hours (a conversion of hydroxylamine: 99.2%).
(Second Tank, the Tank of Excessive Hydroxylamine)
The reaction was conducted until a concentration of cyclododecanone in an organic phase became 0.3% by weight or less. A reaction time was 10 hours (a conversion of cyclododecanone: 98.9%).

Comparative Example 3

A process was conducted as described in Example 9, except that stearic acid was not added.
(First Tank, the Tank of Excessive Cyclododecanone)
The reaction was conducted until a concentration of hydroxylamine sulfate in an aqueous phase became 0.1% by weight or less. A reaction time was 12 hours (a conversion of hydroxylamine: 99.2%).
(Second Tank, the Tank of Excessive Hydroxylamine)
The reaction was conducted until a concentration of cyclododecanone in an organic phase became 0.2% by weight or less. A reaction time was 14 hours (a conversion of cyclododecanone: 99.3%).

The table below shows, in each of Examples and Comparative Examples, the type and the amount of a carboxylic acid or its salt added, a solvent used in oxime-forming and a reaction time for each reaction tank.

TABLE 1

| Example | Carboxylic acid or its salt | Amount of a carboxylic acid or its salt (mol % to CDON) | oxime-formation solvent | First tank[a] (excess CDON) (hr) | Second tank[b] (excess Hx) (hr) |
|---|---|---|---|---|---|
| Example 1 | Caproic acid | 0.1 | Toluene | 4 | 7 |
| Example 2 | Undecanoic acid | 0.1 | Toluene | 4 | 6 |
| Example 3 | Lauric acid | 0.1 | Toluene | 4 | 6 |
| Example 4 | Dodecanedioic acid | 0.05 | Toluene | 4 | 6 |
| Example 5 | Stearic acid | 0.1 | Toluene | 4 | 6 |
| Example 6 | Stearic acid | 0.5 | Toluene | 2 | 3 |
| Example 7 | Sodium laurate | 0.1 | Toluene | 4 | 6 |
| Example 8 | Propionic acid | 0.1 | Toluene | 6 | 9 |
| Comparative Example 1 | None | — | Toluene | 8 | 9 |

TABLE 1-continued

| Example | Carboxylic acid or its salt | Amount of a carboxylic acid or its salt (mol % to CDON) | oxime-formation solvent | First tank[a] (excess CDON) (hr) | Second tank[b] (excess Hx) (hr) |
|---|---|---|---|---|---|
| Comparative Example 2 | Tetrabutylammonium hydrogen sulfate | 0.1 | Toluene | 10 | 7 or more |
| Example 9 | Stearic acid | 0.1 | Isopropyl cyclohexane | 7 | 10 or more |
| Comparative Example 3 | None | — | Isopropyl cyclohexane | 12 | 14 or more |

Note:
CDON: Cyclododecanone,
Hx: Hydroxylamine
[a] In the first tank, a time taken for a concentration of hydroxylamine sulfate in an aqueous phase to be 0.1% by weight or less.
[b] In the second tank, a time taken for a concentration of cyclododecanone in an organic phase to be 0.1% by weight or less.

The invention claimed is:

1. A process for producing cyclododecanone oxime comprising reacting cyclododecanone and an aqueous solution of an inorganic salt of hydroxylamine in the presence of a carboxylic acid in a system consisting of an aqueous phase and a hydrophobic solvent phase,
   wherein the carboxylic acid is at least one selected from the group consisting of undecanoic acid, lauric acid, palmitic acid, stearic acid, arachic acid, dodecanedioic acid, oleic acid, linoleic acid and linolenic acid,
   a pH of the aqueous phase during the reaction is adjusted in the range of 5 or more and less than 6 by adding aqueous ammonia, and the hydrophobic solvent is an aromatic or aliphatic hydrocarbon.

2. The process for producing cyclododecanone oxime according to claim 1, wherein the aqueous solution of an inorganic salt of hydroxylamine is an aqueous solution of hydroxylamine sulfate or hydroxylamine carbonate.

3. The process for producing cyclododecanone oxime according to claim 1, wherein the carboxylic acid is at least one selected from the group consisting of undecanoic acid, lauric acid, stearic acid and dodecanedioic acid.

4. The process for producing cyclododecanone oxime according to claim 1, wherein the carboxylic acid comprises stearic acid, and the hydrophobic solvent comprises at least one selected from the group consisting of toluene and isopropylcyclohexane.

* * * * *